(12) United States Patent
Fischell et al.

(10) Patent No.: US 6,353,754 B1
(45) Date of Patent: Mar. 5, 2002

(54) SYSTEM FOR THE CREATION OF PATIENT SPECIFIC TEMPLATES FOR EPILEPTIFORM ACTIVITY DETECTION

(75) Inventors: David R. Fischell, Fair Haven; Jonathan P. Harwood, Rumson, both of NJ (US)

(73) Assignee: NeuroPace, Inc., Sunnyvale, CA (US)

( * ) Notice: Subject to any disclaimer, the term of this patent is extended or adjusted under 35 U.S.C. 154(b) by 0 days.

(21) Appl. No.: 09/556,415

(22) Filed: Apr. 24, 2000

(51) Int. Cl.$^7$ ................................................. A61B 5/00
(52) U.S. Cl. ...................................................... 600/544
(58) Field of Search ................................... 600/544, 545

(56) References Cited

U.S. PATENT DOCUMENTS 5,995,868 A * 11/1999 Dorfmeister et al. ... 600/545 X
6,016,449 A *  1/2000 Fischell et al. ............. 600/544
6,230,049 B1 *  5/2001 Fischell et al. ............. 600/544

* cited by examiner

Primary Examiner—Robert L. Nasser
Assistant Examiner—Ryan Carter

(57) ABSTRACT

An epileptiform activity patient template creation system is provided which permits the user to efficiently develop an optimized set of patient specific parameters for epileptiform activity detection algorithms. The epileptiform activity patient template creation system is primarily directed to a computer software package which operates within a computer workstation having a processor, disk storage and display for storing, processing and displaying patient EEG signals. The computer processor in conjunction with the software package allows for the marking of the initiation/termination of electrographic seizures within the patient's displayed EEG signals. Epileptiform activity segments are extracted from at least one of the EEG signals with the activity segments including a marked initiation of a seizure. Subsequently, a seizure data set simultaneously displaying a number of the epileptiform activity segments is shown on the display monitor. Epileptiform activity is then detected from the displayed segments by an epileptiform activity detection algorithm having at least one programmable epileptiform activity detection parameter. The template is then created and modified to optimize epileptiform activity detection. The final template can then be downloaded to an implantable neuropacemaker for epileptic seizure control through responsive stimulation.

41 Claims, 11 Drawing Sheets

FIG. 8

SYSTEM FOR THE CREATION OF PATIENT SPECIFIC TEMPLATES FOR EPILEPTIFORM ACTIVITY DETECTION

REFERENCE TO RELATED PATENT APPLICATION

This patent application incorporates by reference the subject matter of Ser. No. 09/517,797 filed on Mar. 2, 2000 entitled "Neurological Event Detection Using Processed Display Channel Based Algorithms and Devices Incorporating These Procedures".

FIELD OF USE

This invention is in the field of systems for the analysis of EEG signals from the brains of human subjects.

BACKGROUND OF THE INVENTION

The current state-of-the-art in workstations for processing EEG signals allows the viewing of either monopole or bipolar montages of electrode inputs. Various seizure detection algorithms have been implemented in such EEG processing workstations to help the epileptologist find epileptiform activity within hours of patient EEG data. In U.S. Pat. No. 6,016,449, Fischell et. al. describes an implantable system for the detection and responsive stimulation to stop neurological events such as epileptic seizures. The Fischell application refers to the use of a physician's workstation for programming a separate implantable device but does not describe the use of a Physician's Workstation as an independent system for patient diagnosis and treatment evaluation. In order for an implantable device for detecting and stopping a neurological event to operate efficiently, it is highly desirable to first determine and test the appropriate epileptiform activity detection algorithm(s) and patient specific detection parameters for each patient using an external workstation.

It is also highly desirable that the patient specific template be programmable into the implantable electrical stimulation therapy device from the workstation. In U.S. patent application Ser. No. 09/517,797, Fischell describes a processed display channel technique for patient specific seizure detection. For each patient, the processed display channel (DC) algorithm(s), detection algorithm(s) used with each PDC and best set of epileptiform activity detection parameters for the chosen detection algorithms together make up the patient specific epileptiform activity detection template. The processed display channel technique described by Fischell does not however describe a streamlined process for picking the best or optimum set of parameters. It is generally necessary to work through hours of EEG data, checking the detection parameters with each marked seizure and then going back to check for false positive detections, which is a tedious and lengthy process. It is highly desirable to provide an automated or semi-automated system that can assist the clinician in finding the optimal epileptiform activity detection algorithm for each patient.

SUMMARY OF THE INVENTION

The present invention is an epileptiform activity patient template creation system that allows the physician to efficiently develop an optimized set of patient specific parameters for one or more epileptiform activity detection algorithms. Such a template once created can be downloaded into an implantable device for seizure control. The epileptiform activity patient template creation system is primarily a computer software package that will run in conjunction with either the programming system for an implantable neuropacemaker or an EEG monitoring and analysis system such as the Physician's Workstation (PWS) described by Fischell in U.S. Pat. No. 6,016,449. Such a workstation can be connected to patients with scalp or intracranial electrodes for acquisition of EEG data or can process previously stored EEG data collected with other EEG data acquisition systems.

Existing EEG monitoring and analysis systems allow the clinician to mark each electrographic seizure and to quickly move through the EEG data from one mark to the next. The present invention provides the additional capability to simultaneously display on a single screen a seizure data set containing all the marked seizures from one or more patient EEG files. In addition, the marked seizures in the seizure data set are time synchronized so that the seizure start mark of all the seizures are vertically aligned on the display. The present invention will work best when less than five signal channels are used for template creation. The Processed Display Channel (PDC) approach described in U.S. patent application Ser. No. 09/517,797 allows the combination of the best EEG channels into one or more PDCs.

A processed display channel (PDC) is a customized combination of specific EEG channels that best show a patient's epileptiform activity. The advantage of processed display channel based epileptiform activity detection is that one or more detection algorithms may be run on processed signals that have been optimized to show epileptiform activity. The fundamental advantage of the optimization is to allow reduction of as many as 128 EEG channels to typically one or two PDCs.

The clinician can choose an epileptiform activity detection algorithm, manually enter a test set of template parameters, verify accurate detection of the multiple marked seizures and then have the system go back to the original EEG files to check for false positive detections.

Once all marked seizures are displayed together on a single screen, a waveform analyzer can be used to graphically show the distribution of algorithm related parameters in a selected segment of the seizure data set signals. The charts displayed can provide a guide for the manual selection of template parameters.

The present invention also has the capability to automatically find the best sets of detection parameters for multiple epileptiform activity detection algorithms and display the accuracy of the selected sets in tabular or graphical form so that the clinician can simply select the best epileptiform activity detection template created by the computer. The computer-selected template can also be adjusted and retested manually by the clinician.

It is understood that EEG is used throughout the following discussions to mean either electroencephlagram data from external scalp electrodes or electrocortigram data from intracranial electrodes. The term brain electrodes are used throughout the following discussions to mean any electrodes within or near the brain including scalp surface electrodes and intracranial electrodes. The term epileptiform activity refers to activity within the brain of a person with epilepsy that is indicative of the disease. Epileptiform activity is present during a clinical epileptic seizure but may also sometimes occur without clinical symptoms.

Thus, it is an object of this invention to provide an epileptiform activity patient template creation system that can simultaneously display a multiplicity of marked electrographic seizures.

Another object of this invention is to provide an epileptiform activity patient template creation system that can simultaneously display a multiplicity of marked electrographic seizures from two or more patient EEG files.

Still another object of this invention is to provide time synchronization of the display of the marked start of a multiplicity of electrographic seizures Still another object of this invention is to implement a PDC based seizure detector within a physician's workstation to provide diagnosis, template creation and testing to optimize the seizure detection means prior to implantation of an implantable electrical stimulation therapy device.

Yet another object of this invention is to provide waveform analysis tools that may be used on EEG or PDC signal segments to provide one of more histograms showing a breakdown of the signal parameters for the selected segment.

Yet another object of this invention is to provide a fully automated means to select the best set of epileptiform activity detector template parameters for a specific patient.

Still another object of this invention is to provide means to download the tested epileptiform activity detection template to an implantable electrical stimulation therapy device.

These and other objects and advantages of this invention will become apparent to a person of ordinary skill in this art upon care full reading of the detailed description of this invention including the drawings as presented herein.

BRIEF DESCRIPTION OF THE DRAWINGS

Figure 8:
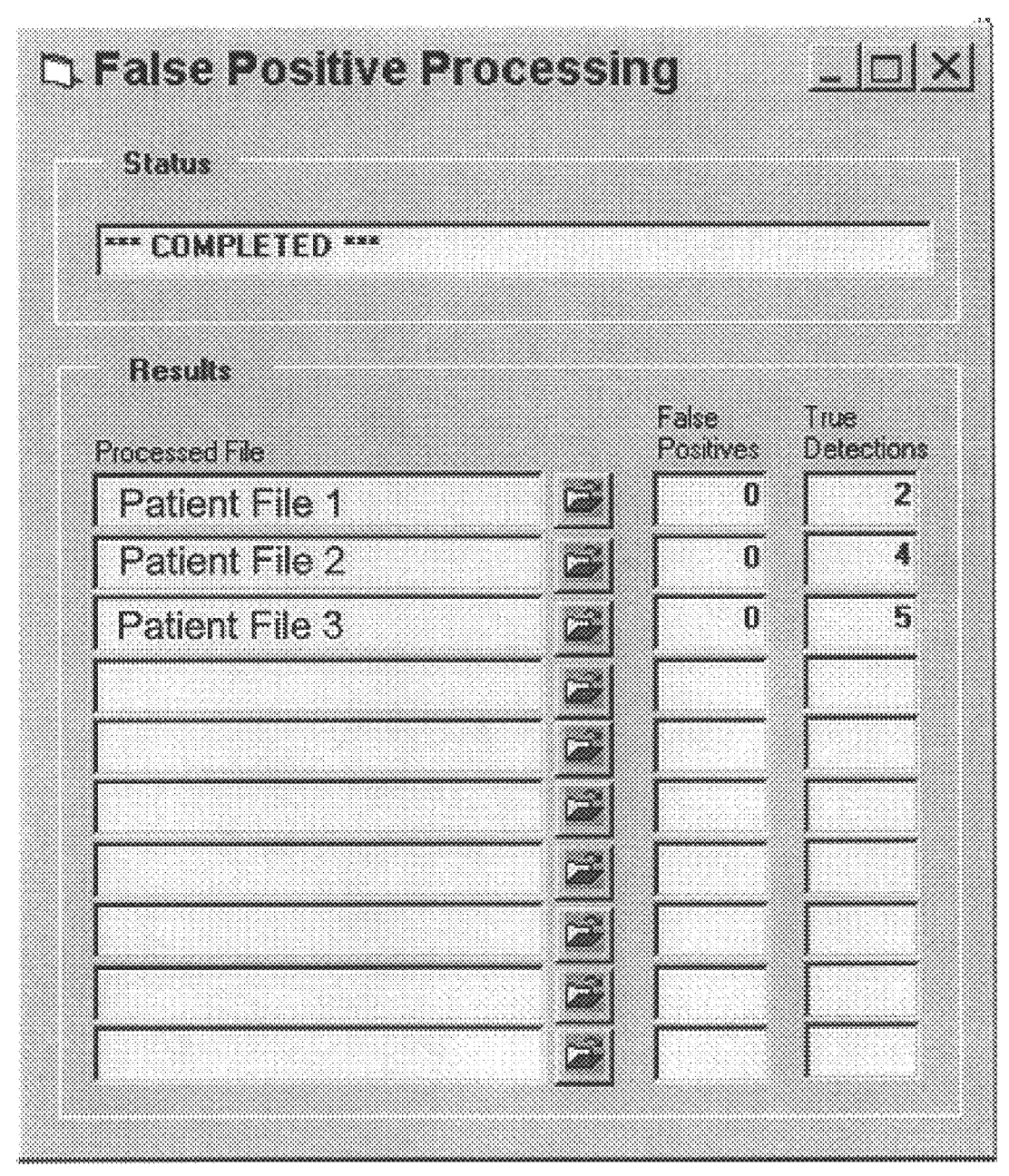

FIG. 8 shows the window displayed on the present invention after it has completed testing of the patient epileptiform activity detection template for valid detections and false positives on the three included patient EEG data files;

DETAILED DESCRIPTION OF THE DRAWINGS

Figure 1:
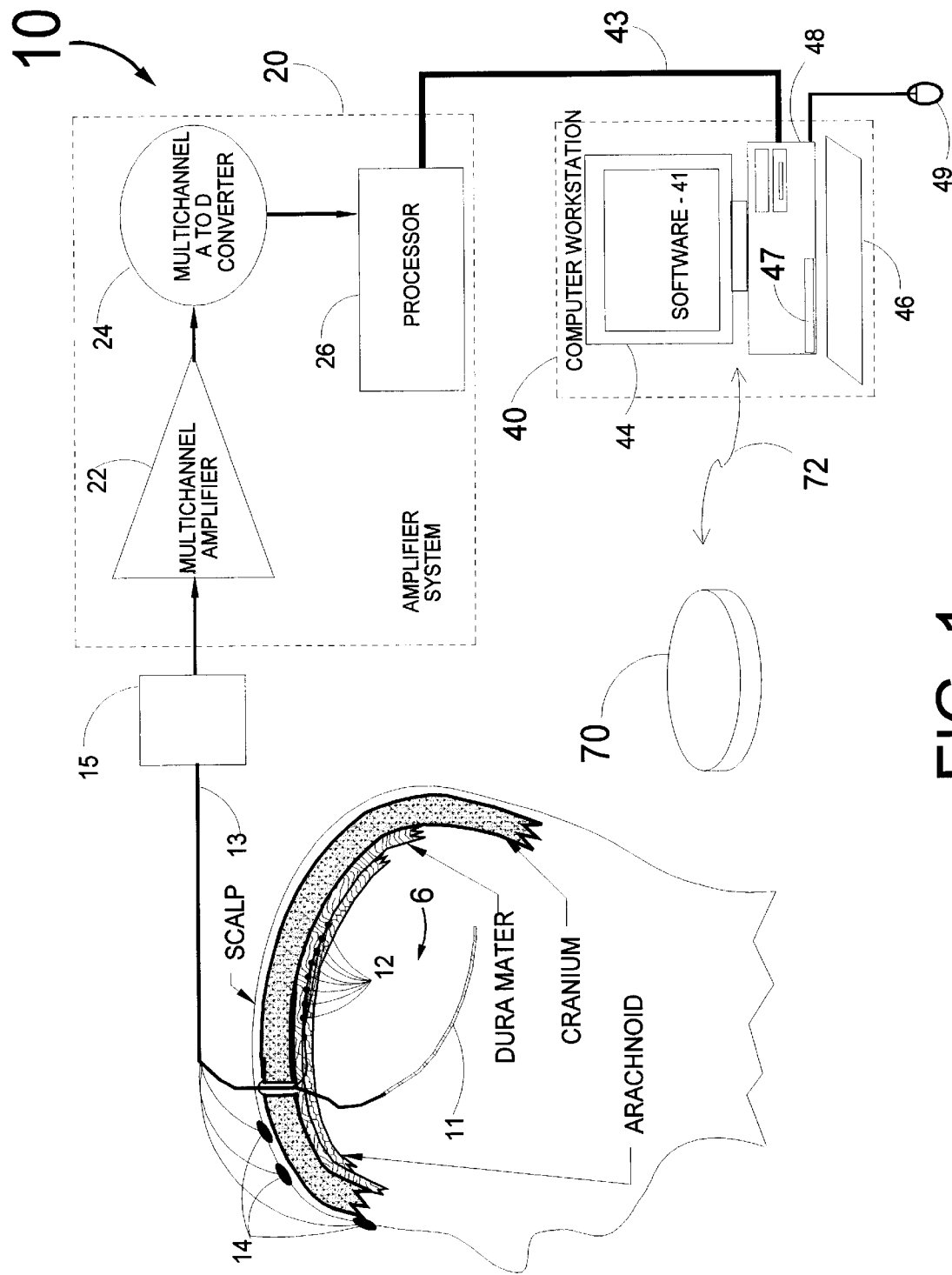
FIG. 1 is a block diagram of computer workstation system for the creation of patient specific epileptiform activity detection templates.

FIG. 1 is a block diagram of a computer workstation 10 having computer workstation hardware 40 running computer workstation software 41. A multiplicity of depth electrodes 11 is implanted deep into the patient's brain. Intracerebral depth electrodes 11, which are often line arrays of electrodes, are useful for recording from or stimulating deep cerebral structures such as the amygdala, hippocampus, cingulate and orbital-frontal regions which deep cerebral structures are characteristically involved in many medically refractory partial epilepsies.

An array of brain surface electrodes 12 is placed above the surface of the patient's brain and may contain more than 100 electrodes. Multiple standard scalp electrodes 14 are attached to the outside of the patient's head. Brain electrodes 6 include the depth electrodes 11, brain surface electrodes 12, scalp electrodes 14 and may include electrodes placed elsewhere under the patient's scalp near or within the brain.

A multi-strand electrode cable 13 connects the scalp electrodes 14, depth electrodes 11 and brain surface electrodes 12 to an electrode interface 15. The electrode interface 15 has connectors for plugging in the electrode leads from the multi-strand cable 13. The electrode interface box connects each plugged in electrode to an amplifier system 20 comprising a multichannel amplifier 22, multi-channel A/D converter 24 and processor 26. The patient's EEG signals coming from the electrode interface box 15 are amplified by the multichannel amplifier 22. After amplification, the signals are digitized by an A/D converter 24 and sent over a standard computer data connection 43 by the amplification system processor 26 to the computer workstation 40. The computer workstation hardware 40 has the capability to send programming over the data connection 43 to the amplifier system 20. Such programming comprises sampling rate, amplifier gain, high, low, notch and band pass filter settings and impedance matching.

The computer workstation 40 is typically a commercially available PC or workstation having a CPU 48, keyboard 46, mouse 49 and monitor 44. The computer workstation software 41 runs under the standard operating system on the commercially available PC or workstation used for the computer workstation 40.

The Synamps manufactured by NeuroScan is an example of a typical amplifier system 20. The standard computer data connection 43 on the Synamps is a Small Computer System Interface (SCSI) cable. A typical CPU 48 would be an Intel Pentium II or Pentium III based PC with a Microsoft Windows NT or Windows 98 operating system with audio and video display capabilities.

When running the computer workstation software 41, the computer workstation 40 can process, store, play back and display on the monitor 44 the patient's EEG signals received from the brain electrodes 6 through the amplification system 20. The computer workstation software 41 also has the capability to detect epileptiform activity. Included in the capability to detect epileptiform activity, the software 41 of the present invention has the capability to allow the clinician to create or modify the patient specific template comprising the algorithms and algorithm parameters for epileptiform activity detection. The patient specific collection of detection algorithms and parameters used for epileptiform activity detection will be referred to throughout the remainder of this specification as the template or patient specific template.

Following development of a patient specific template on the computer workstation 40, the patient specific template would be downloaded through a communications link 72 from the computer workstation 40 to an implantable neuropacemaker 70. The preferred communications link 72 would be a wireless communications link.

The template is used by the implantable neuropacemaker 70 to detect epileptiform activity resulting in responsive stimulation of the patient's brain and data recording of EEG signals before and after the detection for physician review.

Figure 2:
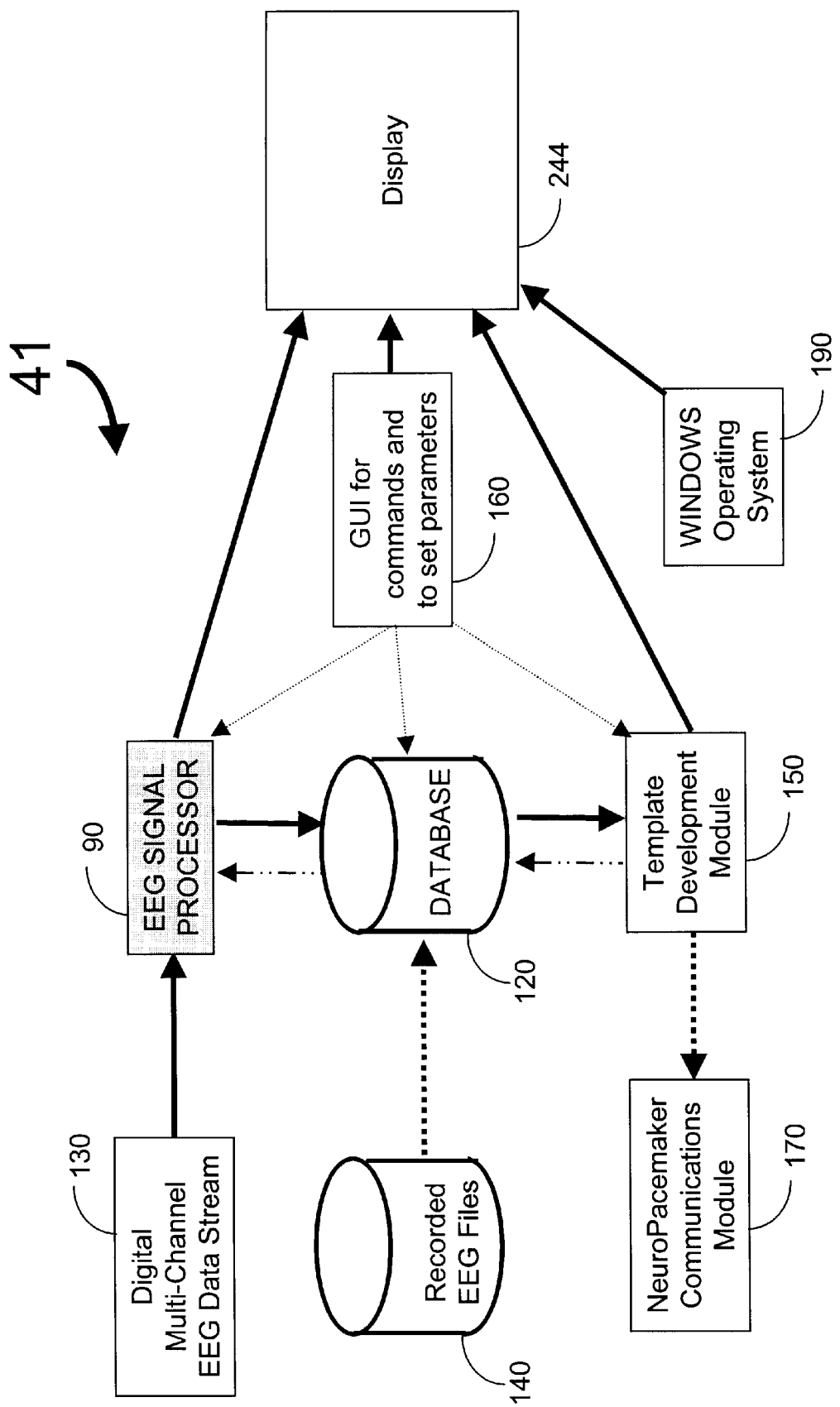
FIG. 2 is a block diagram of the software for an EEG analysis computer workstation system for the creation of patient specific epileptiform activity detection templates.

FIG. 2 shows the architecture of the computer workstation software 10. In this description the term module refers to a unit of software code which carries out a specific function. A module may include processes, subroutines, libraries and other modules.

The CPU 48 of FIG. 1 receives the digital multi-channel EEG data stream 130 over the data link 43 from the amplifier system 20. The digital multi-channel EEG data stream 130 is the input data for the EEG signal processor module 90 which in turn can store and retrieve EEG data from the database 120 and display EEG data on the display 244 which is the image shown on the monitor 44 of the computer workstation 40 of FIG. 1.

A graphical user interface (GUI) 160 provides physician control of the physician's workstation software 41 through menus and toolbars shown on the display 244. The GUI 160 has menus and tool bars to control the EEG signal processor module 90, the, the database 120, the template development module 150, the neuropacemaker communications module 170 and the display 244. The display 244 will also typically show the windows operating system 190 task bar and therefore other windows programs can be run as desired by the system user.

The software 41 is not only capable of processing real time EEG data but can equally well process EEG data stored in the database 120. The stored EEG data may come from the digital multi-channel EEG data stream 130 or may be imported into the database 120 from previously stored EEG files 140. The EEG files 140 may come from a separate EEG data acquisition system (not shown).

Once a collection of EEG data having one or more samples of epileptiform activity has been placed in the database 120 for a specific patient, the template development module 150 can be run in combination with the EEG data display 244 to mark epileptiform activity segments in the patient files and develop a patient specific seizure detection template.

Figure 3:
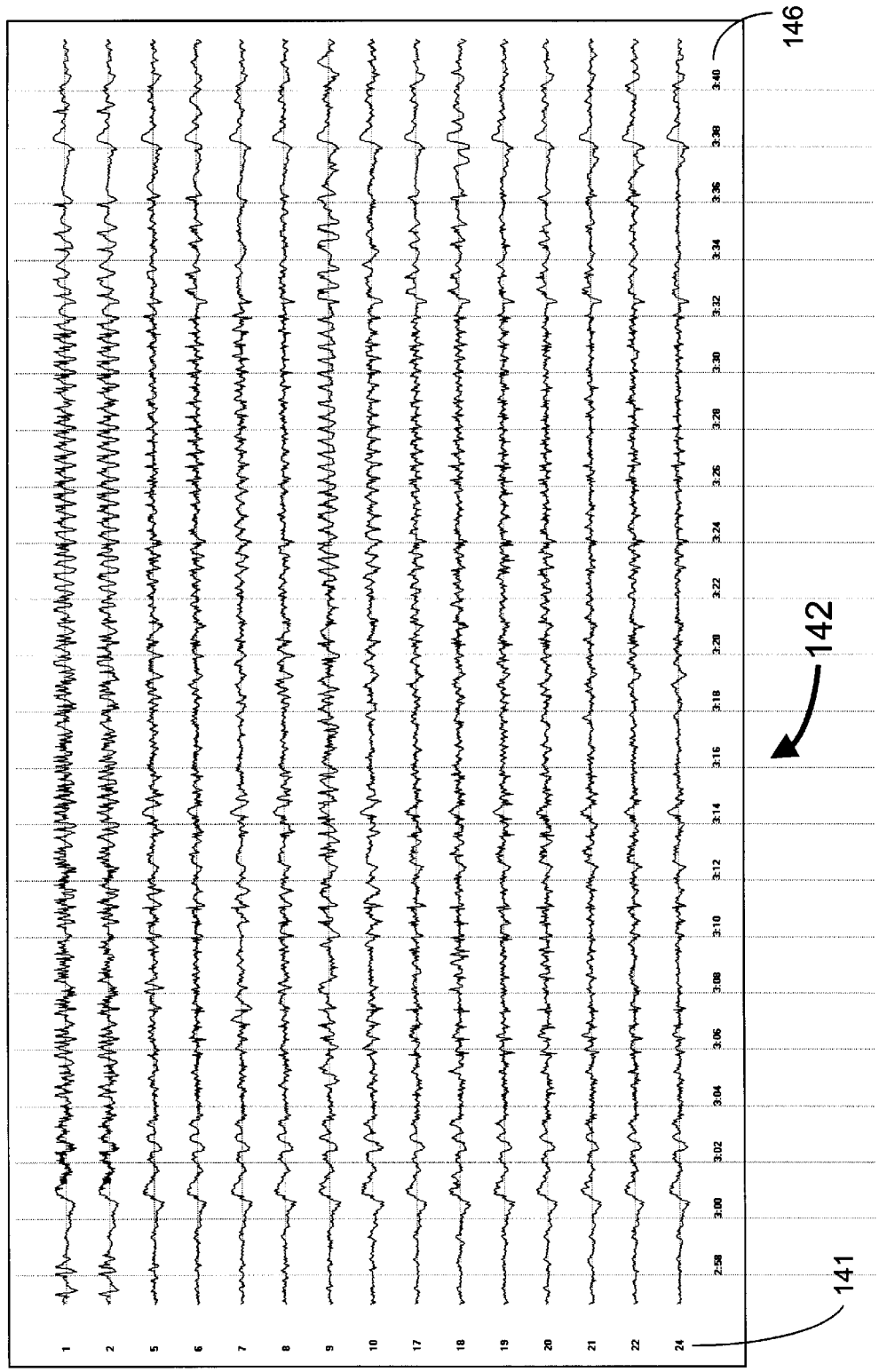
FIG. 3 is a standard multichannel EEG trace showing epileptiform activity.

FIG. 3 shows a multichannel EEG trace 142 as it might be shown on the display 244 of FIG. 2. In the trace 142, not all of the possible EEG channels are shown, some of the channels have been hidden and are not displayed. The channel numbers 141 indicate the EEG channel displayed. The time numbers 146 can show either the actual time or the time from the start of data acquisition. The ability to hide and unhide or recover the specific channels displayed is part of the GUI 160 of FIG. 2.

Figure 4:
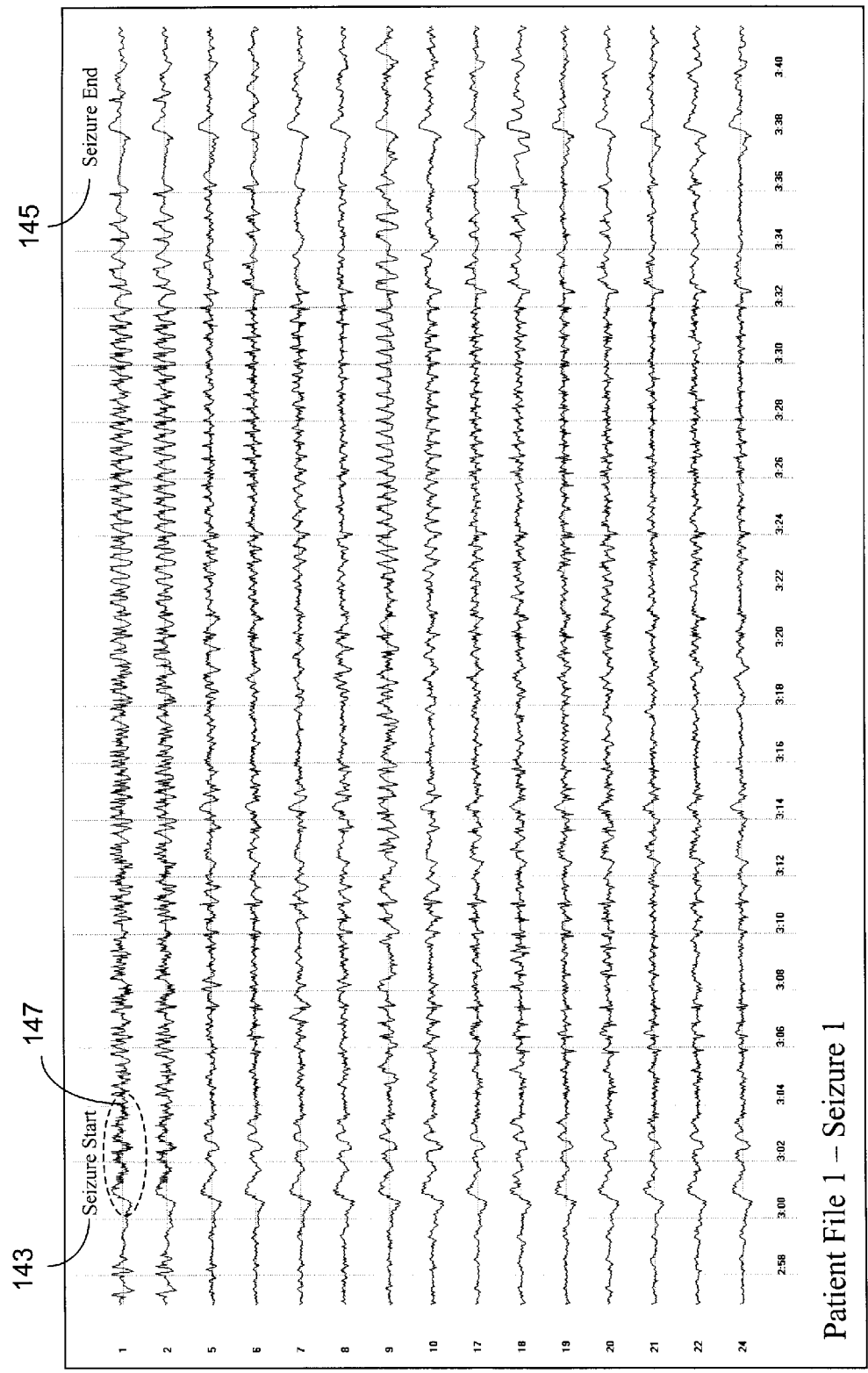
FIG. 4 is the trace of FIG. 1 where the epileptiform activity has been marked with the comments Seizure Start and Seizure End.

FIG. 4 shows a modified multichannel EEG trace 144 that is the same EEG data as in the trace 142 of FIG. 3 with the addition of inserted comments "Seizure Start" 143 and "Seizure End" 145. The first step in the template development process involves the marking of electrographic seizures within one or more stored EEG data files in the database 120 of FIG. 2.

To optimize epileptiform activity detection with the present invention, the user must also select the best single EEG channel or combination of EEG channels to use for epileptiform activity detection. In U.S. patent application Ser. No. 09/517,797, Fischell describes the best single EEG channel or combination of EEG channels to use for epileptiform activity detection as a processed display channel or PDC. All the possible combinations that can be used to create a PDC are well described by Fischell. Fischell also envisions the use of multiple PDCs with detection based on logical operations between valid detections on each PDC.

Looking at the EEG traces of FIG. 4, one can make the choice of a single channel to use for template development. Specifically, channel 1 shows the early onset 147 of the epileptiform activity and would be a good choice as the PDC for this example.

Once all the electrographic seizures have been marked in a stored EEG data file in the database 120 of FIG. 2, the seizure data is ready to be added to the Seizure Data Set. The seizure data set is defined as the patient specific collection of PDC trace segments comprising the multiplicity of marked seizures for that patient. As the template development process continues, each stored EEG data file for a patient will be viewed, the seizures will be marked and added to the seizure data set. When the last EEG data file has been thus processed, the template development module 150 of FIG. 2 is run.

Figure 5:
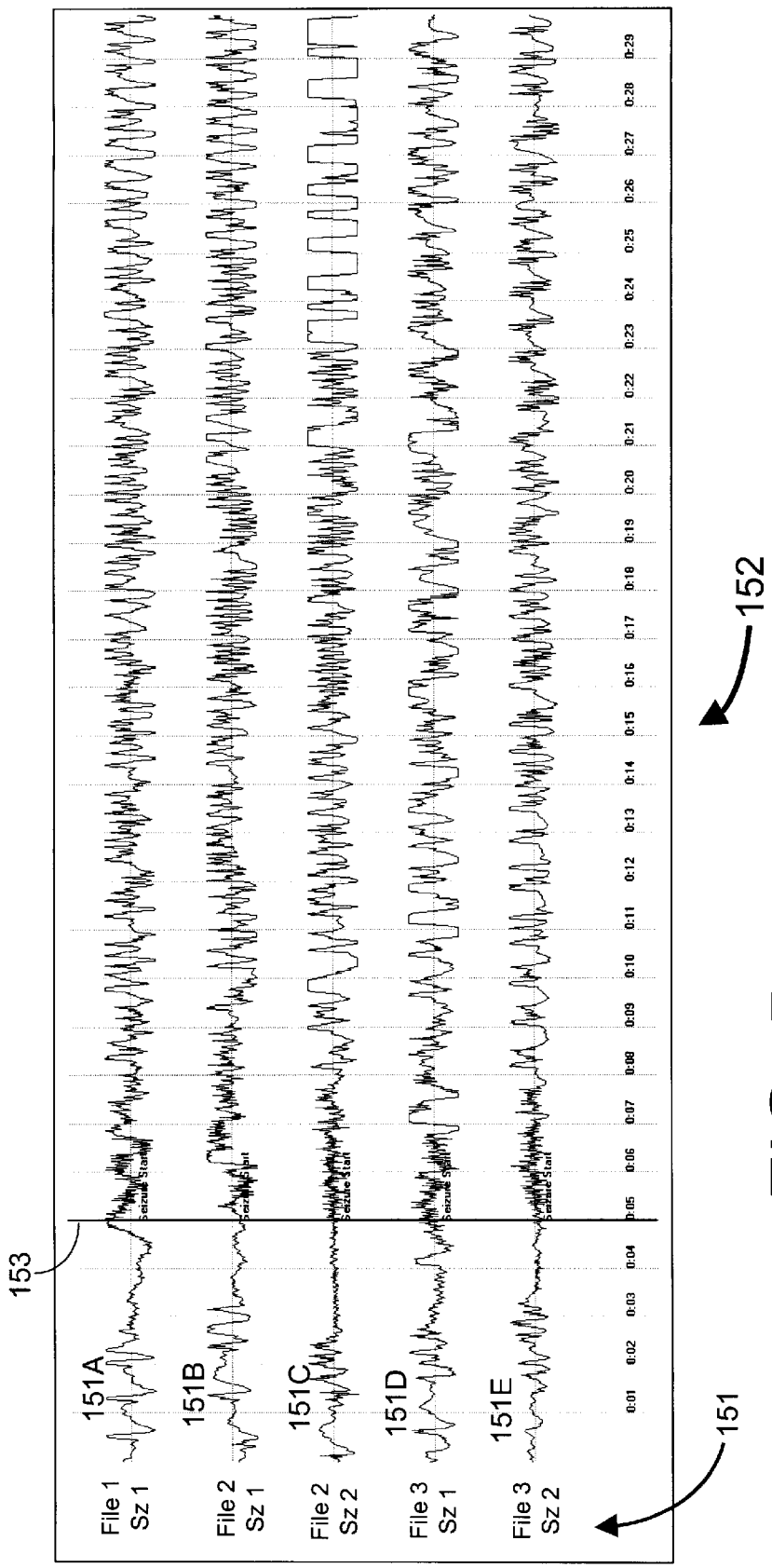
FIG. 5 shows the display of the present invention having a seizure data set with five marked epileptiform activity segments from three different EEG files.

FIG. 5 shows the seizure data set 151 created from three different EEG data files labeled as File 1, File 2 and File 3. File 1 has one marked seizure (Sz1) 151A, File 2 has two marked seizures 151B and 151C and File 3 has two marked seizures 151D and 151E. All five EEG traces are shown one above the other on the template development module display 152. In addition, the seizure start line 153 is used to synchronize in time the marked start of each of the seizures 151A through 151E inclusive.

An important advantage of the present invention over standard EEG viewing systems is the ability to have all of a patient's marked seizures shown one above the other on a single screen. This is particularly beneficial during the development and testing of seizure detection templates. The multiple seizure display 152 also allows the user to identify common features in the onset of each seizure. Onset is used to indicate the first several seconds of epileptiform activity just before or just after the start of an electrographic seizure.

Once the seizure data set 151 has been created, there are two techniques envisioned for producing a template.

1) Manual processing where the algorithm and parameters are selected manually. Each template may be tested after selection for valid detections and false positives.

2) Automated processing where the computer workstation tests multiple sets of parameters within a selected range for one or more algorithms and presents the results for the user to pick the best.

With respect to this application, a false positive detection or false positive is a detection of a feature of an EEG signal by an epileptiform activity detection algorithm where the feature is not true epileptiform activity. The computer workstation software of FIG. 2 can easily be programmed to identify false positives by a detection of epileptiform activity that is not located between the start and end of electrographic seizures marked by the clinician as shown in FIG. 4.

Figure 6:
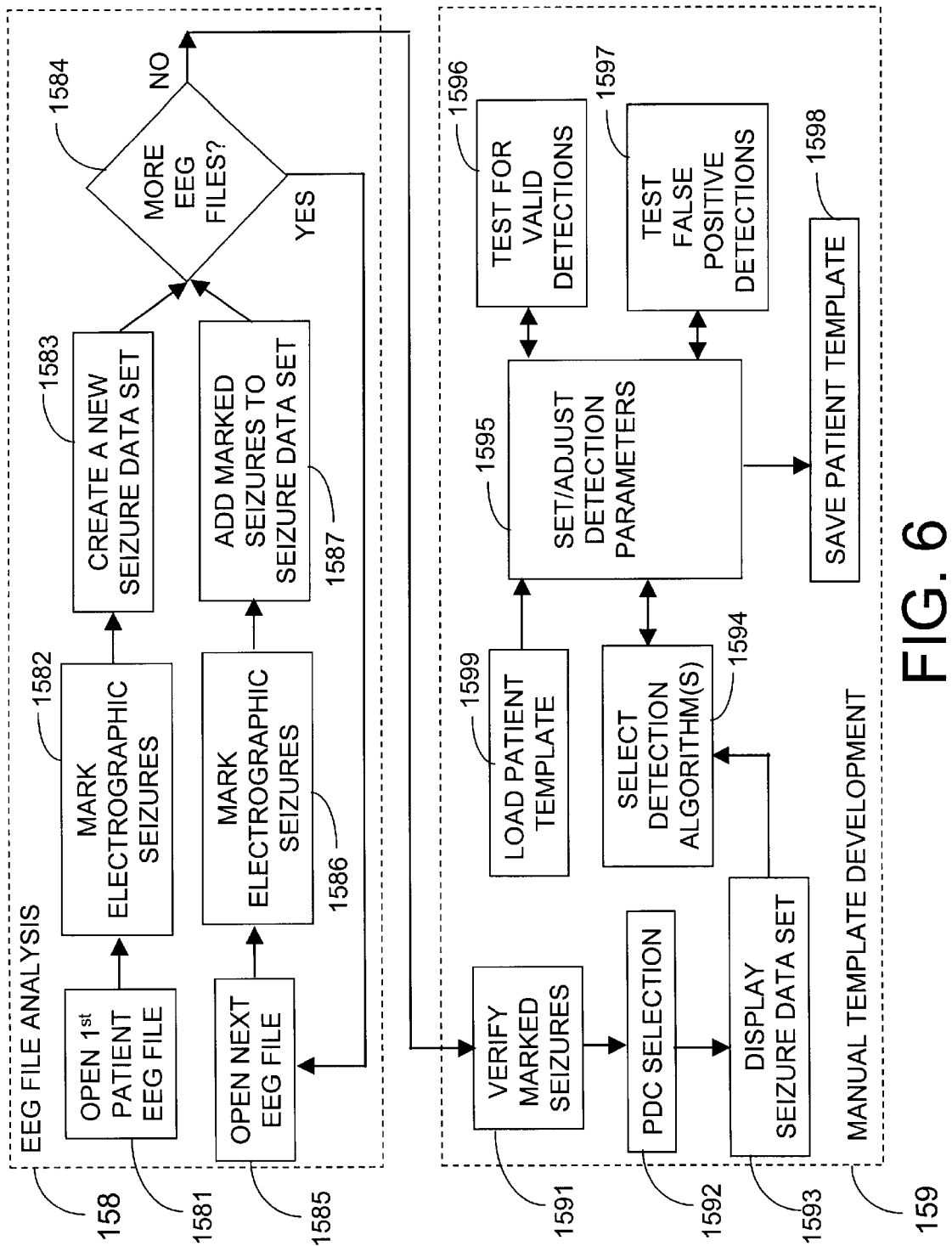
FIG. 6 shows a flow chart for use of the manual process for template development.

FIG. 6 shows a flow chart for use of the manual process 155 for template development. The manual process 155 includes a first stage of EEG file analysis 158 followed by a second stage of template development 159. The EEG file analysis stage comprises the following steps:

1. Open the first EEG file for the patient 1581 using the EEG viewer (see FIG. 3).

2. Manually look through the EEG data and mark the start and end of each electrographic seizure 1582 as shown for the trace 144 of FIG. 4.

3. Through the GUI 160 of FIG. 2, create a new seizure data set 1583 using the marked seizures in the first patient EEG file. It is envisioned that the GUI 160 of FIG. 2 would have buttons or word menu selections to start a new seizure data set using the marked seizures in the current EEG data file.

4. Check if there are no more EEG files to be viewed 1584 go to step 8.
5. If there are more EEG data files, open the next file 1585.
6. Mark the start and end of each electrographic seizure in the current file 1586.
7. Add the newly marked seizures to the seizure data set 1587.
8. GO TO STEP 1 OF THE TEMPLATE DEVELOPMENT STAGE 159.

Figure 7:
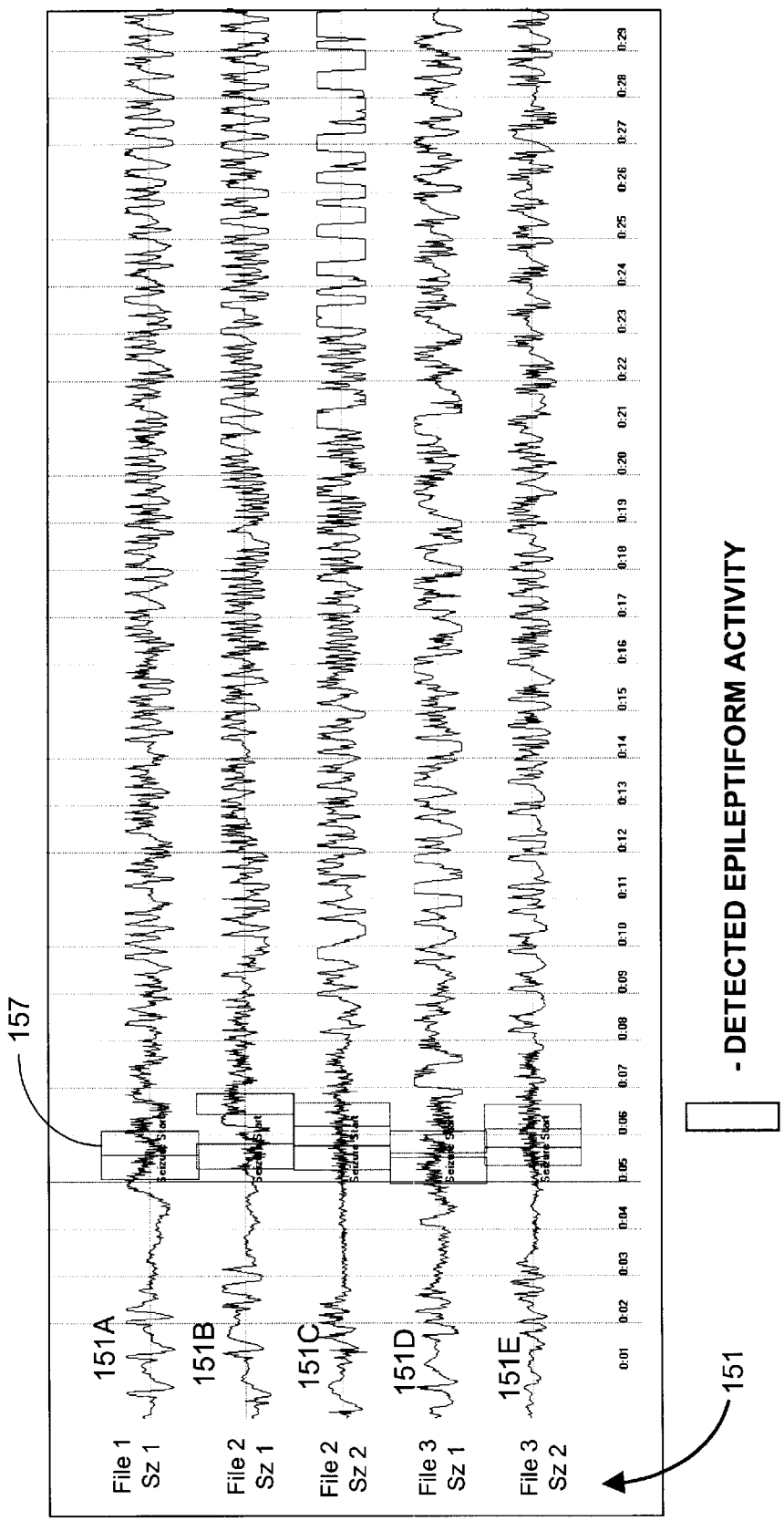
FIG. 7 shows the display of the present invention showing valid seizure detections from the seizure data set with five marked epileptiform activity segments from three different EEG files.

The template development stage 159 allows the user to create, modify and test the patient specific templates for epileptiform activity detection through the following steps:

1. First, verify the marked seizures from the EEG file analysis stage 158 are correct 1591.
2. Select the EEG channel, EEG Channels, or combinations of EEG channels that will be used to form the processed display channels (PDCs) on which the seizure detection algorithms will be tested 1592.
3. The template development module 150 of FIG. 2 will then display the seizure data set 1593 (shown as 151 of FIG. 5) with each marked seizure processed display channel segment (151A through 151E inclusive of FIG. 5) placed one above the other to facilitate the final steps of template development.
4. Select the epileptiform activity detection algorithm or algorithms 1594 to be tested with each of the processed display channels selected in step 1592.
5. Set the detection parameters 1595 for the epileptiform activity detection algorithm or algorithms selected in step 1594. At this point, an initial patient specific template has been created, the template includes the PDC(s) selected in step 1592, the detection algorithm selected in step 1594 and the detection parameters set in step 1595. Previously saved patient templates 1599 can also be loaded directly into step 1595 instead of typing in each parameter. The template is now ready for testing first against the seizure data set displayed in step 1593 and then against the patient EEG data files in which the marked electrographic seizure segments were marked in the EEG file analysis stage 158.
6. Test 1596 the chosen set of detection parameters from step 1595 with the epileptiform activity detection algorithm or algorithms selected in step 1594 on the processed display channel segments as displayed in step 1593.
7. Adjust the template including detection parameters 1595 and/or detection algorithms 1594 until the test 1596 detects each of the marked electrographic seizures close to the marked onset (Seizure Start 143 of FIG. 4). An example of this is shown in FIG. 7 where the template development module 150 of FIG. 2 has drawn rectangles 157 on the seizure data set 151 to indicate valid detections of epileptiform activity.
8. Test the adjusted patient specific template for false positives 1597 against the original EEG data files opened in the EEG file analysis stage 158.
9. Adjust the template including detection parameters 1595 and/or detection algorithms 1594 so that there is a minimum of false positive detections from step 1597 while the test 1596 still detects each of the marked electrographic seizures close to the marked onset (Seizure Start 143 of FIG. 4). FIG. 8 shows an example of the display of the result of the false positive test 1597 for the seizure data set 151 of FIGS. 5 and 7. The result shown in FIG. 8 with multiple true detections and no false positives is an indication of an acceptable template.
10. Save the final patient specific template in step 1598.

The manual template development process is now complete. The saved template can be downloaded to an implantable neuropacemaker 70 of FIG. 1 or can be used during the next EEG data acquisition using the computer workstation 40 of FIG. 1 to check real time detection prior to downloading the template to the neuropacemaker 70.

Figure 9:
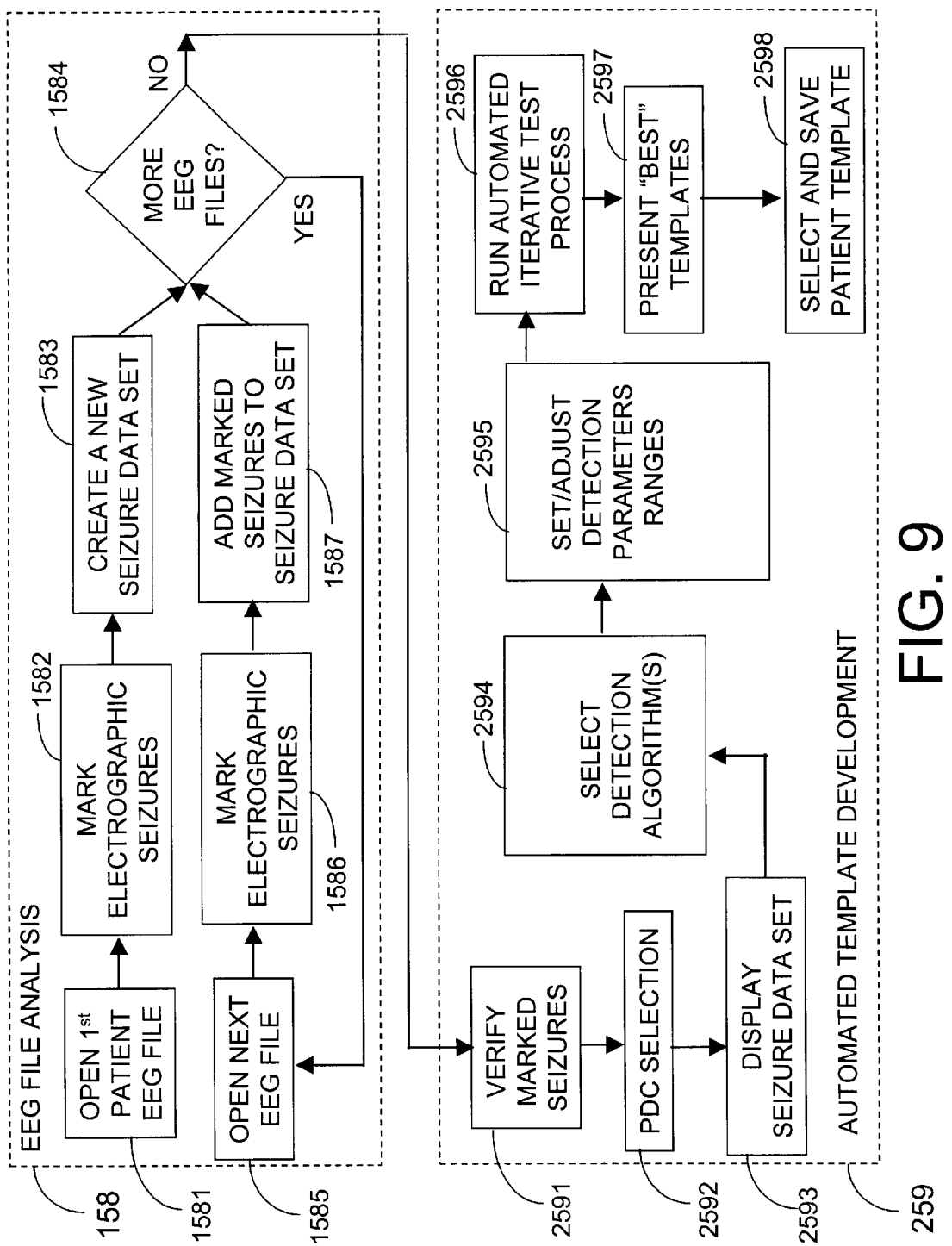
FIG. 9 shows a flow chart for use of the automated process for template development.

FIG. 9 shows a flow chart for use of the automated process 255 for template development. Similar to the manual process 155 of FIG. 6, the automated process 255 includes a first stage of EEG file analysis 158 followed by a second stage of template development 159. The EEG file analysis stage comprises the following steps:

1. Open the first EEG file for the patient 1581 using the EEG viewer (see FIG. 3).
2. Manually look through the EEG data and mark the start and end of each electrographic seizure 1582 as shown for the trace 144 of FIG. 4.
3. Through the GUI 160 of FIG. 2, create a new seizure data set 1583 using the marked seizures in the first patient EEG file. It is envisioned that the GUI 160 of FIG. 2 would have buttons or word menu selections to start a new seizure data set using the marked seizures in the current EEG data file.
4. Check if there are no more EEG files to be viewed 1584 go to step 8.
5. If there are more EEG data files, open the next file 1585.
6. Mark the start and end of each electrographic seizure in the current file 1586.
7. Add the newly marked seizures to the seizure data set 1587.
8. GO TO STEP 1 OF THE AUTOMATED TEMPLATE DEVELOPMENT STAGE 259.

The automated template development stage 259 has the computer workstation 40 of FIG. 1 iteratively test multiple sets of epileptiform activity detection parameters for one or more seizure detection algorithms. The result being to present the user with one or more "best" templates for detection of seizures within several seconds of the marked seizure start line 153 in the seizure data set 151 of FIG. 5. Each seizure detection algorithm, such as those proposed by Fischell in U.S. patent application Ser. No. 09/517,797, would have a different iterative step-by-step process to find the "best" template or templates. The automated template development process 259 would have the following steps:

1. First, verify the marked seizures from the EEG file analysis stage 158 are correct 2591.
2. Select the EEG channel, EEG Channels, or combinations of EEG channels that will be used to form the processed display channels (PDCs) on which the seizure detection algorithms will be tested 2592.
3. The template development module 150 of FIG. 2 will then display the seizure data set 2593 (shown as 151 of FIG. 5) with each marked seizure processed display channel segment (151A through 151E inclusive of FIG. 5) placed one above the other to facilitate the final steps of template development. The user would then select automated template development from either a menu or a tool bar button of the GUI 160 of FIG. 2.

4. When automated template development is selected, the dialog box 255 shown in FIG. 10 would appear. The user would then select the epileptiform activity detection algorithm or algorithms 2594 to be tested with each of the processed display channels selected in step 2592. An example of this selection would be through use of buttons 254A through 254D inclusive in the dialog box 255 of FIG. 10.

Figure 10:
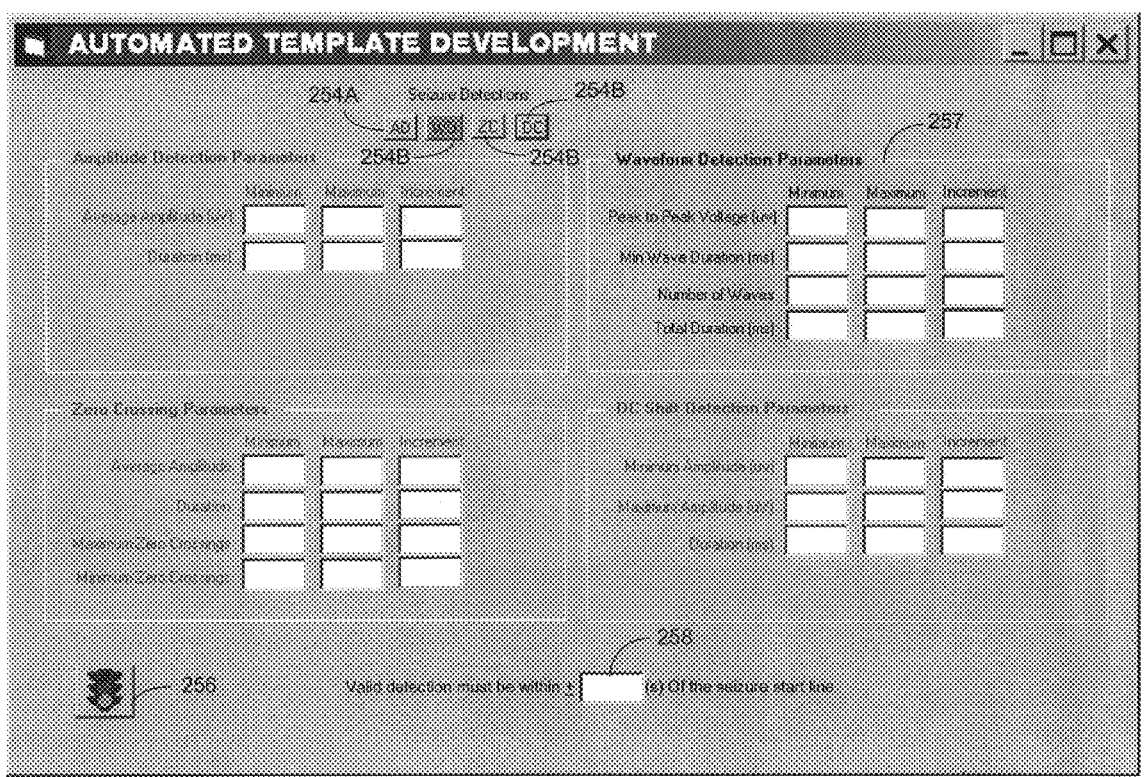
FIG. 10 shows a window showing waveform detection parameters, DC shift detection parameters, amplitude detection parameters, as well as zero crossing parameters; and, FIG. 11 is a flow block diagram showing iterative test processing of a waveform detection algorithm.

5. Set the range of detection parameters 2595 for the epileptiform activity detection algorithm or algorithms selected in step 2594. A dialog box as shown in FIG. 10 in a window created by the GUI 160 of FIG. 2 on the display 244 would have the places to enter the minimum, maximum and increment for each parameter for the selected algorithm or algorithms. The dialog box would also have a button 256 that would start the iterative test process 2596 to find the "best" template or templates for epileptiform activity detection.

6. When enabled the iterative test process 2596 will in a specific order, increment each of the parameters for the selected detection algorithm from step 2594 and test the resulting template for valid detections and for false positives. The automated template development process 259 will then present the "best" template or templates 2597 found. To be a presented by step 2597, the template must result in accurate detection of each and every seizure within several seconds of the seizure start line and no false positive detections of epileptiform activity from the base EEG data files.

7. The user would then select and save one or more or the best templates in step 2598.

8. At this point, the patient specific template has been created, the template includes the PDC(s) selected in step 2592, the detection algorithm selected in step 2594 and the detection parameters set in step 1595.

The automated template development process is now complete. Additional modification and testing of the saved template or templates from step 2598 can be done through the manual template development process 158 as shown in FIG. 6. The manual template development process 158 has the capability to load a saved patient template (step 1599 of FIG. 6).

The saved template can be downloaded to an implantable neuropacemaker 70 of FIG. 1 or can be used during the next EEG data acquisition using the computer workstation 40 of FIG. 1 to check real time detection prior to downloading the template to the neuropacemaker 70.

Figure 11:
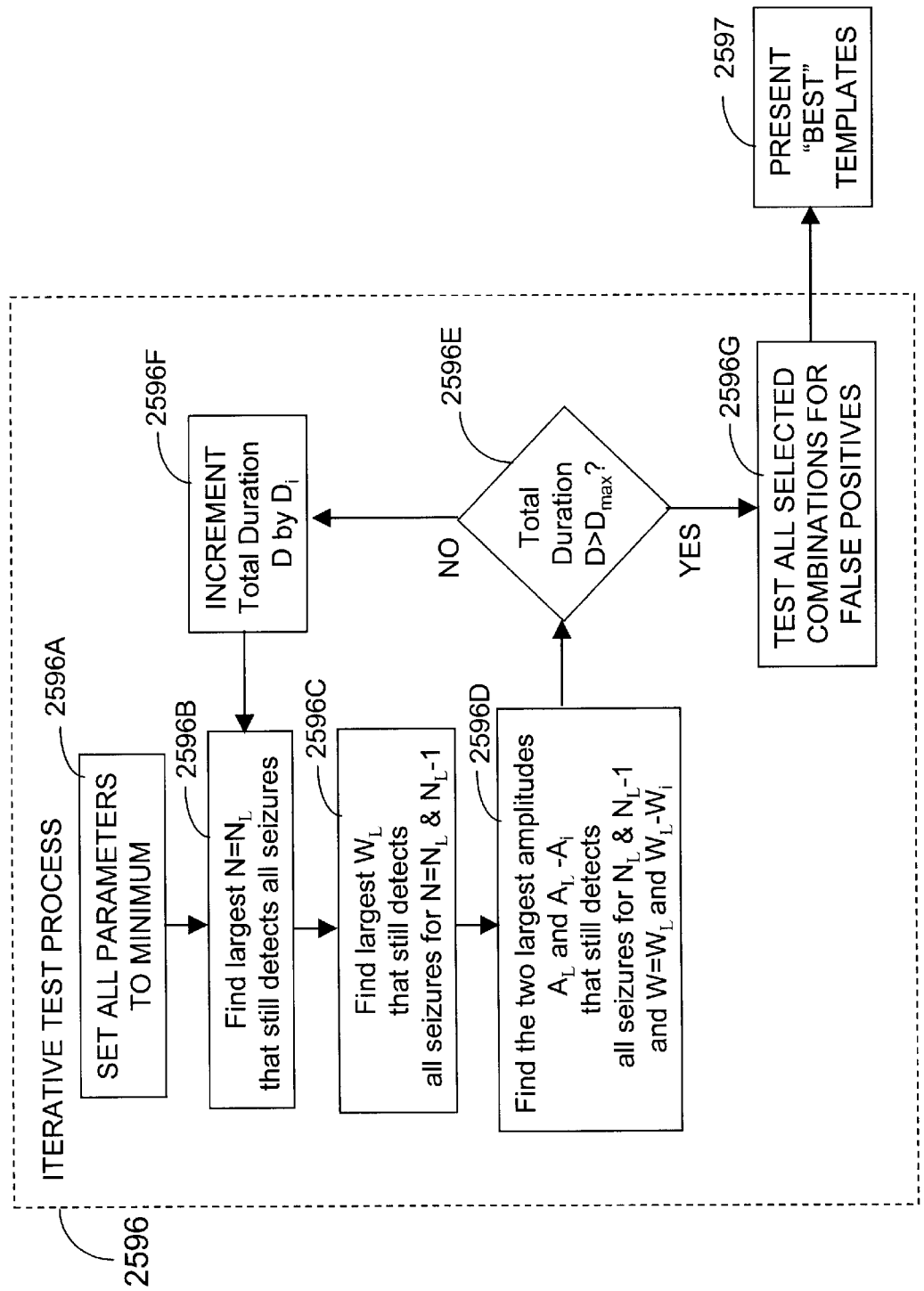

FIG. 11 is an example of the iterative test process 2596 for the waveform detection algorithm described by Fischell in U.S. patent application Ser. No. 09/517,797. The waveform detection algorithm breaks a signal into half waves. Each half wave has amplitude, and half wave duration. The waveform detector counts the number of half waves in a total duration time D having an amplitude greater than the peak-to-peak voltage A and a half wave duration longer than half of the minimum wave duration W. For a seizure detection to be valid the counted number of half waves in the time D must be greater than or equal to twice the preset number of waves N.

FIG. 10 shows the dialog box 255 with Waveform Detection Parameters section 257 having twelve individual boxes for entry of the minimum, maximum and increment range settings for automated template development using the waveform detector algorithm. These parameters are the peak-to-peak voltage A, the minimum wave duration W, the number of waves N and the total duration D. FIG. 10 also has a data entry box 258 for the time limit that governs how close detection must be to the seizure start line 153 of the seizure data set 151 in FIG. 5 to be counted as a valid detection the iterative test process 2596.

In FIG. 11 the range settings will be $A_{min}$, $A_{max}$ and $A_i$ for the minimum, maximum and increment peak-to-peak voltage, $W_{min}$, $W_{max}$ and $W_i$ for the minimum, maximum and increment minimum wave duration, $N_{min}$, $N_{max}$ and $B_i$ for the minimum, maximum and increment number of waves and $D_{min}$, $D_{max}$ and $D_i$ for the minimum, maximum and increment total duration time.

The following steps shown in FIG. 11, are an example of the use of the iterative test process 2596 with the waveform detector.

1. The first step 2596A in the iterative test process 2596 for the waveform detection algorithm described above is to set all the parameter to their minimum values.

2. Next in step 2596B find the largest $N=N_L$ (if any) for which every seizure is detected within the allowed time from the seizure start line 153 of FIG. 5.

3. Next in step 2596C using $N=N_L$ and $N=N_L-1$ as the values for N, increment the minimum wave duration W from $W_{min}$ to $W_{max}$ insteps of $W_i$ to find the largest $W=W_L$ (if any) for each of the two values of N where every seizure is detected within the allowed time from the seizure start line 153 of FIG. 5.

4. Next in step 2596D using $N=N_L$ and $N=N_L-1$ as the values for N, and $W=W_L$ and $W=W_L-W_i$ as the values for W increment the peak-to-peak voltage A from $A_{min}$ to $A_{max}$ insteps of $A_i$ to find the two largest values $A=A_L$ and $A=A_L-A_i$ (if any) for each value of N and W where every seizure is detected within the allowed time from the seizure start line 153 of FIG. 5. There are now at most eight templates (sets of parameters) that will detect every seizure within the allowed time from the seizure start line 153 of FIG. 5.

5. In step 2596, E and F increment the total duration time D by Di and repeat steps 3 and 4 and 5 until D is greater than $D_{max}$.

6. There are now at most eight templates for each value of the total duration time D. in step 2596G Each of these templates is now tested against the original EEG data files to identify false positive detections. All templates tested for false positives would have already shown perfect detection of each marked seizure 151A through 151E of the seizure data set 151 of FIG. 5.

7. The "best" templates would then be presented in tabular form in 2597 of the automated template development process 259. The criteria for inclusion in the "best" templates could be:
   a. All templates resulting in no false positives
   b. The templates for each value of the total duration D with the lowest number of false positives.
   c. The most restrictive sets of parameters (i.e. those using only the largest values $N_L$, $W_L$ and $A_L$ that show no false positives for any value of D.

The best templates can as previously described, be saved for further tweaking using the manual template development process 159 or for actual real time use with an implanted neuropacemaker 70 or a computer workstation 40 as shown in FIG. 1.

Various other modifications, adaptations, and alternative designs are of course possible in light of the above teachings. Therefore, it should be understood at this time that within the scope of the appended claims the invention might be practiced otherwise than as specifically described herein.

What is claimed is:

1. A system for formation and testing of a template for the detection of epileptiform activity from a patient's brain comprising:

a computer workstation having processor means, disk storage means and display means for storing, processing and display of a multiplicity of EEG signals;

said processor means including:

means for marking an initiation and termination of electrographic seizures within said multiplicity of displayed EEG signals;

means for extracting epileptiform activity segments from at least one EEG signal, each of said epileptiform activity segments including a marked initiation of each of said electrographic seizures;

means for simultaneously displaying a seizure data set having a multiplicity of said epileptiform activity segments on said display means;

means for detecting epileptiform activity having at least one programmable epileptiform activity detection parameter; and, means for creation and modification of a template for epileptiform activity detection, said template including patient specific data parameters.

2. The system for formation and testing of a template as recited in claim 1 wherein said patient specific data parameters include the selection of at least one of said multiplicity of said EEG signals processed for epileptiform activity detection.

3. A system for formation and testing of a template as recited in claim 1 wherein said patient specific data parameters include a predetermined epileptiform activity detection parameter applied by said means for detecting said epileptiform activity.

4. The system for formation and testing of a template as recited in claim 1 wherein said multiplicity of EEG signals are stored in EEG files, said seizure data set including epileptiform activity segments from at least two EEG files.

5. The system for formation and testing of a template as recited in claim 1 wherein said computer workstation processor means displays said multiplicity of marked epileptiform activity segments in substantially aligned and vertically ascending position on said display means.

6. The system for formation and testing of a template as recited in claim 1 wherein said processor means includes means for iteratively testing a multiplicity of seizure detection templates, said processor means further including means for displaying an optimized set of templates wherein said optimization is determined by said iterative testing by said processor means.

7. The system for formation and testing of a template as recited in claim 1 wherein said means for detecting epileptiform activity, detects said epileptiform activity on a process display channel formed from at least one of said EEG signals.

8. The system for formation and testing of a template as recited in claim 1 wherein said means for detecting epileptiform activity detects said epileptiform activity on a process display channel formed by summing at least two of said EEG signals.

9. The system for formation and testing of a template as recited in claim 1 wherein said means for detecting epileptiform activity detects said epileptiform activity on a process display channel formed from a signal wherein a first EEG signal is subtracted from at least a second EEG signal.

10. The system for formation and testing of a template as recited in claim 1 wherein said means for detecting epileptiform activity includes means for detecting wave forms.

11. The system for formation and testing of a template as recited in claim 5 wherein said processor means includes means for aligning said initiation of each of said marked seizure segments as displayed in substantially vertical alignment on said display means.

12. The system for formation and testing of a template as recited in claim 11 wherein said processor means includes means for providing a vertical seizure start line for display and highlighting said substantially vertically aligned initiations of each seizure segment on said display means.

13. The system for formation and testing of a template as recited in claim 1 wherein said processor means includes means for manually inserting said seizure detection parameters for input to said processor means for detecting epileptiform activity.

14. The system for formation and testing of a template as recited in claim 13 wherein said processor means further includes means for testing said manually entered set of seizure detection parameters for determining the initiation of said electrographic seizures.

15. A system for formation and testing of a template for the detection of epileptiform activity from a patient's brain comprising:

a computer workstation having processor means, disk storage means, and display means for storing, processing and displaying a multiplicity of EEG signals;

said processor means including:

means for marking an initiation and termination of electrographic seizures within said multiplicity of said displayed EEG signals;

means for extracting epileptiform activity segments from at least one EEG signal, each of said epileptiform activity segments including a marked initiation of each of said electrographic seizures; and, means for detecting epileptiform activity having at least one programmable epileptiform activity detection parameter.

16. The system for formation and testing of a template as recited in claim 15 wherein said processor means further includes means for simultaneously displaying a seizure data set having a multiplicity of said epileptiform activity segments on said display means.

17. The system for formation and testing of a template as recited in claim 15 wherein said processor means further includes means for forming and modifying said template for epileptiform activity detection from patient specific data parameters derived from said EEG signals.

18. The system for formation and testing of a template as recited in claim 17 wherein said patient specific data parameters include the selection of at least one of said multiplicity of said EEG signals being processed for epileptiform activity detection.

19. The system for formation and testing of a template as recited in claim 16 wherein said patient specific data parameters include a predetermined epileptiform activity detection parameter applied by said means for detecting said epileptiform activity.

20. The system for formation and testing of a template as recited in claim 18 wherein said multiplicity of EEG signals are stored in EEG files, said seizure data set including epileptiform activity segments from at least two of said EEG files.

21. The system for formation and testing of a template as recited in claim 15 wherein said computer workstation processor means includes means for displaying said multiplicity of marked epileptiform activity segments in substantially vertical alignment on said display means.

22. The system for formation and testing of a template as recited in claim 21 wherein said processor means provides means for aligning the initiation of each marked seizure segment being displayed in vertically consecutive alignment on said display means.

23. The system for formation and testing of a template as recited in claim 22 wherein said processor means includes means for forming a seizure start line highlighted on said display means for highlighting the aligned in initiation of each said seizure segment on said display means.

24. A system for formation and testing of a template for the detection of epileptiform activity from a patient's brain comprising:
    a computer workstation having processor means, disk storage means and display means for storing, processing and displaying a multiplicity of EEG signals;
    said processor means including:
        means for marking an initiation and termination of electrographic seizures within said multiplicity of displayed EEG signals; and,
        means for extracting epileptiform activity segments from at least one EEG signal, each of said epileptiform activity segments including a marked initiation of each of said electrographic seizures.

25. The system for formation and testing of a template as recited in claim 24 including means for detecting epileptiform activity having at least one programmable epileptiform activity detection parameter.

26. The system for formation and testing of a template as recited in claim 24 wherein said processor means further includes means for simultaneously displaying a seizure data set having a multiplicity of said epileptiform activity segments on said display means.

27. The system for formation and testing of a template as recited in claim 25 wherein said processor means further includes means for forming and modifying said template for epileptiform activity detection from patient specific data parameters derived from said EEG signals.

28. The system for formation and testing of a template as recited in claim 27 wherein said patient specific data parameters include portions of at least one of said multiplicity of said EEG signals being processed for epileptiform activity detection.

29. The system for formation and testing of a template as recited in claim 27 wherein said patient specific data parameters include a predetermined epileptiform activity detection parameter applied by said means for detecting said epileptiform activity.

30. The system for formation and testing of a template as recited in claim 28 wherein said multiplicity of EEG signals are stored in EEG files, said seizure data set including epileptiform activity segments from at least two of said EEG files.

31. The system for formation and testing of a template as recited in claim 24 wherein said computer workstation processor means includes means for displaying said multiplicity of marked epileptiform activity segments in substantially vertical alignment on said display means.

32. The system for formation and testing of a template as recited in claim 31 wherein said processor means provides means for aligning the initiation of each marked seizure segment being displayed in vertically consecutive alignment on said display means.

33. The system for formation and testing of a template as recited in claim 32 wherein said processor means includes means for forming a seizure start line highlighted on said display means for highlighting the aligned initiation of each said seizure segment on said display means.

34. A method for the formation of a template for the detection of epileptiform activities from a patient's brain including the steps of:
    acquiring a multiplicity of EEG signals from said patient's brain;
    storing said multiplicity of said EEG signals in at least one EEG file in a computer workstation having processor means, disk storage means and display means for storing, processing and display of a multiplicity of EEG signals;
    determining the initiation and termination of electrographic seizures in said EEG signals stored in said at least one EEG file;
    marking said initiation and termination of said electrographic seizures in said EEG signals in said at least one EEG file;
    establishing seizure data segments extracted from said at least one EEG signal wherein each of said segments includes said marked initiation of said electrographic seizure; and,
    displaying said seizure data segments on said display means of said computer workstation.

35. The method for development of a template as recited in claim 34 wherein said step of establishing said seizure data segments includes the step of processing said seizure data set for determination of epileptiform activity detection.

36. The method for development of a template as recited in claim 35 wherein said step of storing said multiplicity of EEG signals is followed by the step of processing said at least one EEG file for determination of a epileptiform activity within said EEG signals.

37. The method for the development of a template as recited in claim 36 wherein said processing of said at least one EEG file includes the step of identifying false positive detections.

38. The method for the development of a template as recited in claim 37 wherein said step of identifying false positive detections includes the step of detection of epileptiform activity external to the range of said initiation and termination of said electrographic seizures.

39. The method for the development of a template as recited in claim 35 including the step of processing at least one of said multiplicity of EEG signals for determining an epileptic seizure.

40. The method for the development of a template as recited in claim 35 wherein said step of displaying said seizure data set includes the step of aligning each of said seizure data segments in a vertical manner on said display means.

41. The method for the development of a template as recited in claim 35 wherein the step of displaying said seizure data includes the step of marking the initiation of the electrographic seizures in said segments of said seizure data set.

* * * * *